(12) United States Patent
Kealey et al.

(10) Patent No.: US 7,413,878 B2
(45) Date of Patent: Aug. 19, 2008

(54) RECOMBINANT HOST CELLS EXPRESSING ATOAD AND CAPABLE OF MAKING A POLYKETIDE USING A STARTER UNIT

(75) Inventors: James T. Kealey, San Anselmo, CA (US); Linda C. Dayem, San Anselmo, CA (US); Daniel V. Santi, San Francisco, CA (US)

(73) Assignee: Kosan Biosciences, Inc., Hayward, CA (US)

( * ) Notice: Subject to any disclaimer, the term of this patent is extended or adjusted under 35 U.S.C. 154(b) by 565 days.

(21) Appl. No.: 10/621,206

(22) Filed: Jul. 15, 2003

(65) Prior Publication Data

US 2004/0096946 A1    May 20, 2004

Related U.S. Application Data

(60) Provisional application No. 60/396,513, filed on Jul. 15, 2002.

(51) Int. Cl.
*C12P 19/62* (2006.01)

(52) U.S. Cl. ............................ 435/76; 435/7.1; 435/76; 435/252

(58) Field of Classification Search ........................ None
See application file for complete search history.

(56) References Cited

U.S. PATENT DOCUMENTS

| 6,627,427 B1 | 9/2003 | Katz et al. |
| 6,939,691 B1 | 9/2005 | Khosla et al. |
| 7,011,959 B1 | 3/2006 | Santi et al. |

FOREIGN PATENT DOCUMENTS

| WO | WO 97/02358 | 1/1997 |
| WO | WO 99/03986 | 1/1999 |
| WO | WO 01/27306 | 4/2001 |
| WO | WO 01/31035 | 5/2001 |
| WO | WO 01/31049 | 5/2001 |
| WO | WO 02/068613 | 9/2002 |

OTHER PUBLICATIONS

Long et al. (Molecular Microbiology, vol. 43, No. 5, pp. 1215-1225, 2002).*
U.S. Appl. No. 60/358,939, filed Feb. 22, 2002, Santi et al.
Blattner, F.R. et al. (1997). "The Complete Genome Sequence of *Escherichia coli* K-12," *Science* 277:1453-1468.
Chapman-Smith, A. et al. (1994). "Expression, Biotinylation and Purification of a Biotin-Domain Peptide From the Biotin Carboxy Carrier Protein of *Escherichia coli* Acetyl-CoA Carboxylase," *Biochem. J.* 302:881-887.
Dayem, L.C. et al. (2002). "Metabolic Engineering of a Methylmalonyl-CoA Mutase-Epimerase Pathway for Complex Polyketide Biosynthesis in *Escherichia coli*," *Biochemistry* 41:5193-5201.
Kozak, M. (1991). "Structural Features in Eukaryotic mRNAs That Modulate the Initiation of Translation," *The Journal of Biological Chemistry* 266(30):19867-19870.
Link, A.J. et al. (1997). "Methods of Generating Precise Deletions and Insertions in the Genome of Wild-Type *Escherichia coli*: Application to Open Reading Frame Characterization," *J. Bacteriol.* 179(20):6228-6237.
Pfeifer, B.A. et al. (2001). "Biosynthesis of Complex Polyketides in a Metabolically Engineered Strain of *E. coli*," *Science* 291:1790-1792.
Rodriguez, E. and Gramajo, H. (1999). "Genetic and Biochemical Characterization of the α and β Components of a Propionyl-CoA Carboxylase Complex of *Streptomyces coelicolor* A3(2)," *Microbiology* 145:3109-3119.
Vallari, D.S. et al. (1987). "Regulation of Pantothenate Kinase by Coenzyme A and Its Thioesters." *The Journal of Biological Chemistry* 262(6):2468-2471.

* cited by examiner

*Primary Examiner*—Hope A Robinson
(74) *Attorney, Agent, or Firm*—Townsend and Townsend and Crew LLP

(57) ABSTRACT

Host cells, such as *E. coli*, are provided with an expression system for making starter units required for biosynthesis of polyketides using the ato pathway.

17 Claims, 1 Drawing Sheet

FIG. 1A
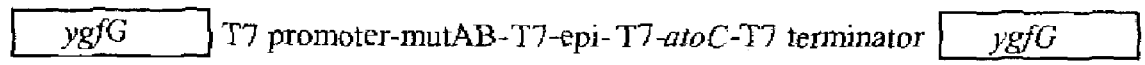
FIG. 1B
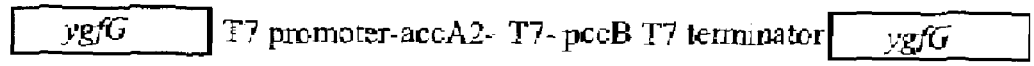
FIG. 1C
T7 promoter-mutAB-T7-epi- T7-*atoC*-T7 terminator

US 7,413,878 B2

RECOMBINANT HOST CELLS EXPRESSING ATOAD AND CAPABLE OF MAKING A POLYKETIDE USING A STARTER UNIT

CROSS-REFERENCE TO RELATED APPLICATIONS

This patent application claims benefit of U.S. provisional patent application No. 60/396,513, filed Jul. 15, 2002, which is incorporated herein by reference.

STATEMENT REGARDING FEDERALLY SPONSORED RESEARCH

This invention was supported in part by Grant No. AI151106, National Institutes of Health. The U.S. government may have certain rights in this invention.

FIELD OF THE INVENTION

The present invention provides methods and materials for producing polyketides by providing host cells with an expression system for making starter units required for biosynthesis of polyketides. Polyketides are a diverse class of compounds with a wide variety of activities, including activities useful for medical, veterinary, and agricultural purposes. The present invention therefore relates to the fields of molecular biology, chemistry, recombinant DNA technology, medicine, animal health, and agriculture.

BACKGROUND OF THE INVENTION

The ability to control aspects of polyketide biosynthesis has stimulated interest in the combinatorial engineering of novel antibiotics. Given the difficulty in producing polyketide compounds by traditional chemical methodology, and the typically low production of polyketides in wild-type cells, there has been considerable interest in finding improved or alternate means to produce polyketide compounds. For example, there has been interest in making polyketides in host cells that are otherwise unable to make polyketides. E. coli host cells, among other host cells which do not otherwise make polyketides, have been contemplated that incorporate expressions systems for expressing polyketides synthases to make polyketides. See PCT publication No. 01/27306 which is incorporated herein by reference.

Polyketide biosynthesis involves the condensation of malonyl CoA, methylmalonyl CoA, or related substituted malonyl CoA precursors, also known as "extender units," onto an acetyl CoA, propionyl CoA, or related acyl CoA precursor, also known as a "starter unit." Of the myriad host cells possible for utilization as polyketide producing hosts, many do not naturally produce such substrates (i.e., polyketide precursors) or do not produce the substrates (i.e., polyketide precursors) in adequate amounts. For example, E. coli does not produce methylmalonyl CoA in sufficient quantities for polyketide synthesis using methylmalonyl CoA as a substrate (precursor). The introduction and modification of biochemical pathways for methylmalonyl CoA biosynthesis in host cells that do not otherwise make polyketides have also been contemplated. See PCT publication Nos. 01/27306 and 01/31035, which are incorporated herein by reference. Two biochemical pathways involving methylmalonyl CoA are relevant to the present invention as well. These pathways are the methylmalonyl CoA mutase pathway, hereafter referred to as the MUT pathway, and the propionyl CoA carboxylase pathway, hereafter referred to as the PCC pathway. See PCT/US 02/06399.

Although approaches to make polyketide in organisms that otherwise do not make polyketides, or make them in low quantities, are extremely useful, it would be useful to produce polyketides that differ from naturally occurring polyketides by incorporating different starter units not found in naturally occurring polyketides.

Interest in making non-natural polyketides has led to organisms that produce polyketides using modified modular polyketide synthase systems wherein directed modification incapacitates the system from using its natural starting material. Novel polyketides have been synthesized by overriding the starter module and supplying a variety of suitable diketide substrates in the form of NAC thioesiers or other suitable thioester. See PCT patent publication Nos. 97/02358 and 99/03986, each of which is incorporated herein by reference. In particular, 15-methyl-6-deoxyerythronolide B (15-methyl-6-dEB) can be made using a 6-dEB synthase (DEBS) gene, by feeding a propyl diketide thioester (e.g., (2S,3R)-3-hydroxy-2-methylhexanoate N-acetylcysteamine thioester) to DEBS. The resulting polyketide, 15-methyl-6-dEB, is also referred to as 13-propyl-6-dEB because it has a propyl group at the 13-position replacing the ethyl group found in 6-dEB. While the diketide feeding technology provides useful amounts of compound, the cost of producing polyketides by that technology is increased by the need to prepare the synthetic diketide. Moreover, certain polyketide producing cells degrade some of the diketide before it can be incorporated into a polyketide by the PKS, thus increasing the cost of production. Methods to produce polyketides by other means could be more efficient and cost effective, therefore, if the need to feed costly synthetic diketide substrates to the PKS were eliminated, in order to produce non-naturally occurring polyketides.

Given the potential for making valuable and useful novel polyketides in large quantities in heterologous host cells, there is a need for host cells capable of making the substrates (i.e., precursors) required for novel polyketide biosynthesis. The present invention helps to meet this need by providing recombinant host cells that contain a PKS expression system, and that also contain one or more expression systems for making substrates (i.e., precursors) for novel polyketide biosynthesis.

SUMMARY OF THE INVENTION

The present invention provides recombinant host cells and expression vectors for precursors and polyketide synthase (PKS) for producing polyketides, e.g., novel polyketides, in host cells that are otherwise unable to make those polyketides due to the lack of an operable biosynthetic pathway to produce a precursor required for biosynthesis of polyketides and due to a lack of a PKS expression system. The present invention also provides methods for increasing the amounts of a polyketide produced in a host cell by providing recombinant biosynthetic pathways for production of a precursor utilized in the biosynthesis of a product, and the recombinant host cells containing these recombinant biosynthetic pathways.

In one aspect, the invention provides a recombinant host cell capable of making a polyketide using a starter unit, where the recombinant host cell is derived from a native host cell by modification with an expression vector, and where the native host cell is incapable of producing the starter unit and the expression vector expresses one or more enzymes that catalyze the synthesis of the starter unit, or the native host cell produces the starter unit and the expression vector overexpresses one or more proteins whose expression results in increased production of the starter unit. In some embodiments, the expression vector expresses or overexpresses the atoAD enzyme, which catalyzes the transfer of a CoA from a CoA thioester to an acid or carboxylate in order to provide an alternate CoA thioester starter unit. For example, the AtoAD transferase catalyses the CoA transfer from acetyl CoA to butyrate resulting in a butyryl CoA starter unit. In some embodiments, the expression vector expresses or overexpresses a positive transcription regulator that increases the expression of the atoAD enzyme. In some of these embodiments the positive transcription regulator is the atoC protein.

In particular, one embodiment of the present invention is directed to a recombinant host cell capable of making a non-naturally occurring polyketide from a polyketide synthase (PKS) using a precursor required for biosynthesis of the polyketide in the host cell, wherein the host cell is modified with an expression vector for expressing an enzyme that produces the precursor, or is modified with an activated endogenous gene for expressing the enzyme, wherein the host cell, in the absence of the enzyme, is unable to make the polyketide.

If the host cell does not have an endogenous expression system for a PKS, the host cell is provided with such a PKS expression system for making a polyketide. In a preferred embodiment, the polyketide is synthesized by either a modular, aromatic, or fungal PKS. In another preferred embodiment, the PKS is a modular PKS, preferably 6-deoxyerythronolide B synthase (DEBS). The polyketide produced by the host cell of the invention containing the PKS generally differs from the usual product produced by the PKS in that the precursor naturally used as the starter unit for the polyketide is replaced by a different precursor.

Thus, in some embodiments, the invention provides recombinant host cells comprising one or more expression vectors that drive expression of the enzymes that produce a polyketide precursor. In another embodiment, the invention provides a recombinant host cell that comprises not only an expression vector of the invention but also an expression vector that comprises a promoter positioned to drive expression of a PKS. In a related embodiment, the invention provides recombinant host cells comprising the vector that produces the PKS and its corresponding polyketide.

In some embodiments, the host cell is further modified to express methylmalonyl-CoA mutase and methylmalonyl-CoA epimerase. These host cells may be further modified in certain embodiments to overexpress a B12 transporter gene, e.g., a B12 transporter gene that is endogenous to *E. coli*. In some of these embodiments, the host cell is in media that facilitates B12 uptake.

In other embodiments, the host cell is further modified to express propionyl-CoA carboxylase. These host cells may be further modified to overexpress a biotin ligase enzyme, which in some embodiments is encoded by the birA gene. In some embodiments, the host cell is modified to express sleeping beauty mutase and methylmalonyl-CoA epimerase.

In a preferred embodiment, the host cell is modified with an expression system that provides starter units other than propionyl CoA. Generally, the natural starter unit precursor is propionyl CoA, and the starter unit host cells of the invention is acetyl CoA, butyryl CoA, 3-fluoropropionyl CoA, 3-chloropropionyl CoA, 3,3,3-trifluoropropionyl CoA, 3-hydroxypropionyl CoA, fluoroacetyl CoA, lactyl CoA, (methylthio)acetyl CoA, chloroacetyl CoA, glycolyl CoA, 4-chlorobutyryl CoA, 2-methylbutyryl CoA, or valeryl CoA. In some embodiments, the starter unit is butyryl CoA or (methylthio)acetyl CoA. In a preferred embodiment, the polyketide utilizes butyryl CoA in its biosynthesis. In one preferred embodiment, the polyketide is synthesized by a modular PKS that requires butyryl CoA to synthesize the polyketide.

In some embodiments, the recombinant host cells of the invention are capable of producing a polyketide that is an analog of 6-deoxyerythronolide B (6-dEB) modified by replacement of the propionate starter unit, where the polyketide is 14-desmethyl-6-dEB, 15-methyl-6-dEB, 15-fluoro-6-dEB, 15-chloro-6-dEB, 15-trifluoro-6-dEB, 15-hydroxy-6-dEB, 14-desmethyl-14-fluoro-6-dEB, 14-hydroxy-6-dEB, 14-desmethyl-14-(methylthio)-6-dEB, 14-desmethyl-14-chloro-6-dEB, 14-desmethyl-14-hydroxy-6-dEB, 15-(chloromethyl)-6-dEB, 14-ethyl-6-dEB, or 15-ethyl-6-dEB. In some embodiments, the polyketide is 15-methyl-6-dEB or 14-desmethyl-14-(methylthio)-6-dEB.

The host cell is either a procaryotic or eukaryotic host cell. In a preferred embodiment, the host cell is an *E. coli* host cell. In another embodiment, the host cell is a yeast host cell. Examples of host cells other than *E. coli* include *Saccharomyces cerevisiae*, *Streptomyces coelicolor* or other *Streptomyces*, *Bacillus subtilis*, and *Myxococcus*. In another embodiment, the host cell is a plant host cell. In a preferred embodiment, the host cell is either an *E. coli* or yeast host cell, the precursor is butyryl CoA, and the polyketide is 13-propyl-6-dEB (i.e., 15-methyl-6-dEB).

In another aspect, the invention provides a recombinant expression vector that comprises an inducible promoter positioned to drive expression of one or more genes that encode the enzymes required for biosynthesis of a polyketide precursor. In a preferred embodiment, the promoter is derived from a PKS gene. In a preferred embodiment, the host cell is an *E. coli* or yeast host cell. In some embodiments, the expression vector is pKOS207-15a, pKOS207-15b, pKOS207-15c, or pKOS207-15d. The invention also provides host cells containing these vectors.

In another aspect, the invention provides a method for producing an analog of 6-deoxyerythronolide B (6-dEB) modified by replacement of the propionate starter unit in a host cell capable of making a polyketide using a starter unit, where the recombinant host cell is derived from a native host cell by modification with an expression vector, and where the native host cell is incapable of producing the starter unit and the expression vector expresses one or more proteins that produce the starter unit, or the native host cell produces the starter unit and the expression vector overexpresses one or more proteins whose expression results in increased production of the starter unit, comprising culturing the host cell under conditions wherein the analog of 6-dEB is produced. In some embodiments, the polyketide produced is 15-methyl-6dEB.

These and other embodiments of the invention are described in more detail in the following description, the examples, and claims set forth below.

BRIEF DESCRIPTION OF THE DRAWING

FIG. 1 illustrates expression cassettes useful in modifying host cells to express or overexpress protein(s) (e.g., enzymes) of metabolic pathways for the production of polyketide precursors.

1A: Mutase/epimerase/atoC integration cassette.
1B: PCC integration cassette.
1C: Mutase/epimerase/atoC cassette.

DETAILED DESCRIPTION OF THE INVENTION (1) Introduction

The present invention provides recombinant host cells and expression vectors for making polyketides from polyketide synthase (PKS) in host cells, which are otherwise unable to make those polyketides due to the lack of a biosynthetic pathway to produce a precursor required for biosynthesis of the product, or which produce the precursors in insufficient quantities (i.e., recombinant host cells modified to increase the native host cells' production of the precursor(s)). In the latter embodiments, recombinant host cells of the invention cause increased production of the precursor at a level that is about two-fold, about five-fold, about ten-fold, about one hundred-fold, or more than about one hundred-fold the level that the native host cell produces under the same culture conditions.

(2) Definitions

The present invention may be better understood with reference to the following definitions. Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

As used herein, 'recombinant' has its ordinary meaning in the art and refers to a nucleic acid synthesized or otherwise manipulated in vitro (e.g., 'recombinant nucleic acid'), to methods of using recombinant nucleic acids to produce gene products in cells or other biological systems, to a polypeptide (e.g., 'recombinant protein') encoded by a recombinant nucleic acids, or to cells comprising a recombinant nucleic acid (including progeny of cells into which a recombinant nucleic acid has been introduced).

As used herein, 'gene' refers to a nucleic acid sequence that encodes a useful product. A gene can encode an mRNA that is transcribed from the gene and translated by a ribosome into a protein.

As used herein, 'heterologous' in reference to a protein in a recombinantly modified cell means a gene or protein not found in an unmodified cell of the same species or strain (e.g., a non-recombinant cell) one example of a heterologous gene is a gene from a first species that is introduced into a cell of a second species (e.g., by introduction of a recombinant polynucleotide encoding the gene). Another example of a heterologous gene is a gene (in a cell) that encodes a chimeric PKS.

As used herein, 'host cell' refers to a prokaryotic or eukaryotic cell that can or has received recombinant vectors bearing one or more genes, e.g., genes that encode proteins involved in the production of polyketide precursors, and/or genes encoding proteins of a polyketide synthase. A 'recombinant host cell' is a host cell that has received a recombinant vector or vectors. A 'native host cell' is a host cell that has not received a recombinant vector but that is capable of receiving a recombinant vector. The term includes progeny of the host cell.

As used herein, a 'precursor' is a molecule used as a building block or source of structural material in the synthesis of another molecule. A 'polyketide precursor' or 'polyketide precursor unit' (used interchangeably herein) is a precursor used in the synthesis of a polyketide. A 'starter' or 'starter unit' (used interchangeably herein) is the first precursor in a series of reactions that results in the synthesis of a final molecule. Generally the term is used herein to refer to polyketide starter units (i.e., the final product is a polyketide), which include without limitation propionyl CoA, acetyl CoA, butyryl CoA, 3-fluoropropionyl CoA, 3-chloro propionyl CoA, 3,3,3-trifluoropropionyl CoA; 3-hydroxypropionyl CoA, 2-fluoroacetyl CoA, 3-azido propionyl CoA, 4-chlorobutyryl CoA, 3-fluorobutyryl CoA, 4-azidobutyryl CoA and the CoA thioesters of the following acids: lactic acid, 2-(methylthio) acetic acid, chloroacetic acid, glycolic acid, 4-chlorobutyric acid, 2-methylbutyric acid, or valeric acid. An 'extender' or 'extender unit' (used interchangeably herein) refers to a precursor other than the starter unit in a series of reactions that results in the synthesis of a final molecule. Generally the term is used herein to refer to polyketide extender units (i.e., the final product is a polyketide), which include without limitation malonyl CoA, methylmalonyl CoA, or related substituted malonyl CoA molecules.

As used herein, 'operably linked,' 'operatively linked' or 'operationally associated' (used interchangeably) refer to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. To optimize expression and/or in vitro transcription, it may be helpful to remove, add or alter 5' untranslated portions of the clones to eliminate extra, potentially inappropriate alternative translation initiation (i.e., start) codons or other sequences that may interfere with or reduce expression, either at the level of transcription or translation. Alternatively, consensus ribosome binding sites (see, e.g., Kozak, *J. Biol. Chem.*, 266:19867-19870 (1991)) can be inserted immediately 5' of the start codon and may enhance expression. The desirability of (or need for) such modification may be empirically determined using techniques known in the art.

As used herein, a protein or a group of proteins 'produce' a product if the protein(s) catalyze a reaction or a series of reactions involved in the synthesis of the product (e.g., one or more enzymes of a metabolic pathway for the synthesis of a product, e.g., a starter unit for a polyketide), or the protein(s) act as regulators of other proteins involved in the synthesis of a product (e.g., a positive transcriptional factor such as atoC).

As used herein, 'overexpression' of a protein refers to expression of the protein in a modified cell (e.g., a recombinant host cell) at levels above those normally found in the unmodified cell (e.g., a native host cell) under the same culture conditions. Generally, overexpression is the result of introduction of an expression vectors containing a gene or genes for the protein into a native cell that contains endogenous genes coding for the same protein or a homologous protein with the same activity (e.g., a homologous enzyme or transcription factor), and expression of the protein(s) coded for by the gene(s) the expression vector. The protein may be expressed at a level that is about 1.5-fold, two-fold, five-fold, ten-fold, one-hundred-fold, or more than about one hundred-fold the levels normally expressed in an unmodified cell.

The present invention may be practiced with reference to this disclosure and conventional methods of molecular biology and recombinant DNA techniques within the skill of one of ordinary skill in the art. Such techniques are explained in the literature, see e.g. *Current Protocols in Molecular Biology* (F. M. Ausubel et al., eds., 1987, including supplements through 2001); *Molecular Cloning: A Laboratory Manual*, third edition (Sambrook and Russel, 2001); *PCR: The Poly-* merase Chain Reaction, (Mullis et al., eds., 1994); *Current Protocols in Immunology* (J. E. coligan et al., eds., 1999, including supplements through 2001).

(3) Description of the Invention

In one aspect, the invention provides a recombinant host cell capable of making a polyketide using a starter unit, where the recombinant host cell is derived from a native host cell by modification with an expression vector, and where the native host cell is incapable of producing the starter unit and the expression vector expresses one or more proteins that produce the starter unit, or the native host cell produces the starter unit and the expression vector overexpresses one or more proteins whose expression results in increased production of the starter unit.

The polyketide is a polyketide synthesized by either a modular, aromatic, or fungal PKS. In a preferred embodiment, the precursor is selected from the group consisting of acetyl CoA, butyryl CoA, 3-fluoropropionyl CoA, 3-chloro propionyl CoA, 3,3,3-trifluoropropionyl CoA, 3-hydroxypropionyl CoA, 2-fluoroacetyl CoA, 3-azido propionyl CoA, 4-chlorobutyryl CoA, 3-fluorobutyryl CoA, 4-azidobutyryl CoA and the CoA thioesters of the following acids: lactic acid, 2-(methylthio) acetic acid, chloroacetic acid, glycolic acid, 4-chlorobutyric acid, 2-methylbutyric acid, or valeric acid. In one preferred embodiment, the polyketide synthase utilizes butyryl CoA in its biosynthesis. In one preferred embodiment, the polyketide is synthesized by a modular PKS that requires butyryl CoA to synthesize the polyketide. In another embodiment, the polyketide synthase utilizes (methylthio)acetyl CoA in its biosynthesis.

Preferably, the polyketide produced is other than 6-dEB. Preferably the polyketide is 15-fluoro-6-dEB (i.e., 13-fluoroethyl-6-dEB), 15-chloro-6dEB (i.e., 13-chloroethyl-6-dEB), 13-propyl-6-dEB (i.e., 15-methyl-6-dEB), 14-desmethyl-6-dEB (i.e., 13-methyl-6-dEB), 15-azido-6-dEB (i.e., 13-azidoethyl-6-dEB), 15-(chloromethyl)-6-dEB (i.e., 13-chloropropyl-6-dEB), 15-(fluoromethyl)-6-dEB (i.e., 13-fluoropropyl-6-dEB), 15-ethyl-6-dEB (i.e., 13-butyl-6-dEB), 15-(azidomethyl)-6-dEB (i.e., 13-azidopropyl-6-dEB), 15-trifluoro-6-dEB, 15-hydroxy-6-dEB, 14-desmethyl-14-fluoro-6-dEB, 14-hydroxy-6-dEB, 14-desmethyl-14-(methylthio)-6-dEB (i.e., 14-methylthio-6-dEB), 14-desmethyl-14-chloro-6-dEB, 14-desmethyl-14-hydroxy-6-dEB, and 14-ethyl-6-dEB. In one embodiment, the polyketide is 13-propyl-6-dEB (i.e., 15-methyl-6-dEB). In another embodiment, the polyketide is 14-desmethyl-14-(methylthio)-6-dEB (i.e., 14-methylthio-6-dEB). In preferred embodiments, the host cells are modified to produce sufficient amounts polyketide precursors to support biosynthesis of polyketides at levels ranging from 1 µg/L, to 1 mg/L, to 10 mg/L, to 100 mg/L, to 1 g/L, to 10 g/L, to more than 10 g/L.

In another preferred embodiment of the invention, the host cell does not use propionyl CoA as a starter unit, and is unable to make 6-dEB. If the cell does not make propionyl CoA from propionate, for example, it will make other acyl-CoAs, such as butyryl CoA from other acyl substrates (i.e., precursors) such as butyrate. In the presence of an expression system for PKS, non-naturally occurring polyketides will be produced that use these alternative acyl CoA starter units, and 6-dEB will not be produced.

The present invention provides recombinant DNA expression vectors and methods for making a polyketide and its required precursors in any host cell. In a preferred embodiment, the host cell is an *E. coli* host cell. In another preferred embodiment, the host cell is a yeast host cell. In another embodiment, the host cell is a plant host cell. In a preferred embodiment, the host cell is either an *E. coli* or yeast host cell, the polyketide is 15-methyl-6-dEB, and the precursor is butyryl CoA.

In one embodiment, advantage is taken of the ato pathway, which is present, for example, in *E. coli* but not normally used to produce polyketide precursors. In accordance with the invention, the genes involved with the ato pathway are overexpressed in organisms such as *E. coli* or are provided in an expression vector. In another embodiment of the invention, the genes involved in the ato pathway are overexpressed in organisms, such as *E coli*, in which the gene for malonyl CoA decarboxylase has been inactivated.

The operon for the ato pathway is found in *E. coli* and thus the structure of the operon is found in the complete genome sequence of *E. coli*. Blattner, et al., *Science*, 277:1453-74 (1997).

In another embodiment of this aspect, homologs of enzymes in the ato pathway are derived from *Bacillus subtilis, Clostridium acetobutylicum, Streptomyces coelicolor*, and *Salmonella typhimurium*.

There are six proteins encoded by this ato pathway operon, although not all are necessary to provide precursors. In a preferred embodiment, use is made of only three proteins encoded by this operon: AtoC, AtoA and AtoD.

atoC encodes a transcriptional regulator (AtoC) which is a positive transcriptional regulator that "turns on" or activates the atoAD gene. The AtoC protein from *E. coli* has 461 amino acids.

atoAD encodes an acetyl-CoA acetoacetate: CoA transferase (AtoAD) which naturally catalyzes the reaction: acetyl CoA+acetoacetate⇌acetate and acetoacetyl CoA, but can also catalyze other reactions where a substrate other than acetoacetate is fed, such as the reaction of acetyl CoA+butyrate⇌acetate and butyryl CoA. The atoAD gene encodes the transferase enzyme 2.8.3.8. (using the numbering system devised by the Nomenclature Committee of the International Union of Biochemistry and Molecular Biology). In *E. coli*, this transferase comprises an α subunit, that is, the AtoD protein having 216 amino acids, and a β subunit, the AtoA protein having 220 amino acids. A number of different organisms contain genes homologous to the *E. coli* atoA and atoD genes which express AtoA and AtoD proteins are of varying sizes. Depending on the host cell employed for production of polyketides, introduction and expression of the atoA and atoD genes from a source other than *E. coli* may be preferred. These source organisms include but are not limited to: *Salmonella typhimurium, Clostridium acetobutylicum, Bacillus subtilis*, and *Streptomyces coelicolor*.

The enzyme encoded by atoAD is demonstrated herein to be promiscuous with respect to substrate in its ability to catalyze the reaction shown above. Thus, in addition to acetoacetate and butyrate as substrates, these enzymes can also utilize acetate, 3-fluoropropionate and 3-chloropropionate and the like. Examples of analogs that can be used as substrates for atoAD in the invention are described above. Thus, these enzymes can be used to provide a variety of starter units for synthesis of desired polyketides.

atoE encodes a small chain fatty acid transporter (AtoE), which may be useful in transporting substrates to those cells that need such transport of substrates. However, atoE is not needed to transport butyrate into an *E. coli* cell. The AtoE protein from *E. coli* has 440 amino acids.

The recombinant expression vectors of the invention comprise an inducible promoter positioned to drive expression of one or more genes that encode the enzymes required for biosynthesis of a precursor (i.e., operatively linked to the genes that encode the enzymes). In a preferred embodiment, the promoter is derived from a PKS gene. In another preferred embodiment, the promoter is one derived from a host cell gene or from a virus or phage that normally infects the host cell and is heterologous to the gene that encodes the biosynthetic enzyme. Promoters such as T7, lac, pBAD, tac, or trc may be used.

In one embodiment, the host cells of the invention have been modified to express a heterologous acetyl-CoA acetoacetate:CoA transferase (AtoAD) for the production of acyl-CoA starter units. In a preferred embodiment, atoAD overexpresses acetyl-CoA acetoacetate:CoA transferase preferably using a promoter such as T7, lac, PBAD, tac or trc.

In one embodiment, the host organism, E. coli for example, has endogenous atoA and atoD genes that are not activated in a homologous organism (i.e., a native host cell), but can be activated by inserting a promoter for atoC which in turn activates homologous (endogenous) atoA and atoD genes to encode the CoA transferase AtoAD. In another preferred embodiment, endogenous atoC is found in E. coli and is activated such that it expresses a positive transcriptional regulator that effects the expression of atoAD. One such activator is AtoS which is a two switch regulator kinase (a sensor kinase) that activates atoC.

In another preferred embodiment, an atoC gene and a promoter are integrated into an organism. The integration of an atoC gene and a promoter in an E. coli host cell that contains endogenous atoC is shown in Example 1. In another embodiment, the host organism does not contain all of the ato pathway genes and at least one or all of the genes must be introduced (e.g., integrated) into the host organism.

In a preferred embodiment, the host cells are E. coli host cells. E. coli host cells do not appear to make butyryl CoA endogenously (see Vallar, David, et al., Journal of Biological Chemistry 262:2468-2471 (1987)), and thus upon feeding of acid substrates the ato pathway can be utilized to make an acyl-CoA, such as butyryl CoA, for use as a starter unit for the production of novel polyketides by polyketide synthases.

In another embodiment, the invention provides a recombinant host cell that comprises not only an expression vector of the invention but also an expression vector that comprises a promoter positioned to drive expression of a PKS. In a related embodiment, the invention provides recombinant host cells comprising the vector that produces the PKS and its corresponding polyketide. In a preferred embodiment, the host cell is an E. coli or yeast host cell.

Neither E. coli nor yeast makes sufficient methylmalonyl CoA to support biosynthesis of large amounts of polyketides that require methylmalonyl CoA extender units in their biosynthesis, and most species do not produce the methylmalonyl CoA substrate (i.e., recursor) at all. In one embodiment, the present invention provides E. coli, yeast, and other host cells that produce methylmalonyl CoA in amounts sufficient to support polyketide biosynthesis. In preferred embodiments, the cells produce sufficient amounts of methylmalonyl CoA to support biosynthesis of polyketides requiring methylmalonyl CoA for their biosynthesis at levels ranging from 1 µg/L; to 1 mg/L, to 10 mg/L, to 100 mg/L, to 1 g/L, to 10 g/L.

Host cells of the invention may also be modified to produce extender units for the synthesis of polyketides. Production of extender units is described in, for example, published P.C.T. patent applications WO 01/31049, WO 01/31035, and WO 01/27306; U.S. provisional patent application No. 60/358, 936, filed Feb. 22, 2002; and U.S. patent application Ser. No. 09/697,022, filed 25 Oct. 2000, Ser. No. 09/699,136, filed 27 Oct. 2000, and Ser. No. 09/687,855, filed 13 Oct. 2000, each of which is incorporated herein by reference. In one embodiment, host cells of the invention are modified to express a heterologous methylmalonyl CoA mutase, as disclosed in published P.C.T. patent application WO 01/31035 and U.S. patent application Ser. No. 09/699,136. This enzyme, which converts succinyl CoA to methylmalonyl CoA (although the reverse reaction is 20 times more favored; boosting the steady-state level of succinyl CoA, which is a TCA cycle intermediate, could further increase methylmalonyl-CoA levels) has been expressed in E. coli using a gene cloned from propionibacteria but was inactive due to the lack of vitamin B12. In accordance with the methods of the present invention, this enzyme can be made in an active form in E. coli and other host cells by either expressing (constitutively or otherwise) a B12 transporter gene, such as the endogenous E. coli gene and/or by utilizing a media that facilitates B12 uptake (as used herein, B12 can refer to the precursor hydroxocobalamin, which is converted to B12). The host cell may also be modified to overexpress the btuR gene, which encodes an enzyme that introduces the adenosyl moiety into mature coenzyme B12 precursors, such as hydroxocobalamin. While certain methylmalonyl CoA mutases make the R-isomer, including the methylmalonyl CoA mutases derived from the propionibacteria, the R-isomer can be converted to the S-isomer using an epimerase. For example, epimerase genes from Propionibacteria or Streptomyces can be employed for this purpose.

In a preferred embodiment, the host cells of the invention have been modified to express a heterologous methylmalonyl CoA mutase and epimerase. Expression is driven by a suitable promoter, such as those described above. In one preferred embodiment, the expression vector contains a Propionibacterium shermanii methylmalonyl CoA mutase (mutAB) gene and a Streptomyces coelicolor methylmalonyl CoA epimerase gene. In a preferred embodiment, the host cells are E. coli host cells, for example the K214-37 strain E. coli host cells, which has been co-transformed with pKOS173-158 and BP130, as shown in Example 1.

In another embodiment, the host cells of the invention have been modified to express an acetyl-CoA acetoacetate:CoA transferase for the production of acyl-CoA starter units and heterologous propionyl CoA carboxylase that converts propionyl CoA to methylmalonyl CoA as disclosed in U.S. patent application Ser. No. 09/687,855, which is incorporated herein by reference. In this embodiment, one can increase the amount of methylmalonyl CoA extender units by culturing the cells in a media supplemented with propionate as shown in Example 2. In a preferred embodiment, the host cells are E. coli host cells, for example the K207-3 strain of E. coli host cells, which has been co-transformed with pKOS214-004, pKOS173-158 and BP130, as illustrated in Example 2.

Other preferred strains and plasmids of the invention include:

| Strain | Plasmid | Description |
| --- | --- | --- |
| k173-145 | — | panD (point mutant in panD gene, abolishing panD activity); T7-sfp, T7-prpE in prp locus |
| K214-37 | — | panD; T7-sfp, T7-prpE in prp locus; T7-mutAB, T-7-epimerase, T7-atoC in ygfg locus |
| k207-3 | — | panD; T7-sfp, T7-prpE in prp locus; T-7 pCCB, T-7-ACCA1 in ygfg locus |
| — | pKOS173-158 | T7-eryA1 on pET expression vector with kanamycin resistance |
| — | BP130 | T7-eryA2, eryA3 on a pET plasmid (ampicillin resistance). |
| — | pKOS214-004 | T7-atoC on pACYC plasmid (tetracycline resistance). |

-continued

| Strain | Plasmid | Description |
|---|---|---|
| — | pKOS207-15a | T7-mutAB, T-7-epimerase, T7-atoC on pACYC plasmid (tetracycline resistance). |
| — | pKOS207-15b | T7-mutAB, T-7-epimerase, T7-atoA, atoD on pACYC plasmid (tetracycline resistance). |
| — | pKOS207-15c | T7-sbm, T-7-epimerase, T7-atoC on pACYC plasmid (tetracycline resistance). |
| — | pKOS207-15d | T7-sbm, T-7-epimerase, T7-atoA, atoD on pACYC plasmid (tetracycline resistance). |

Thus, in accordance with the methods of the invention, the heterologous production of certain polyketides in *E. coli*, yeast, and other host organisms require both the heterologous expression of a desired PKS and also the enzymes that produce at least some of the substrate (i.e., precursor) molecules required by the PKS. These substrate (i.e., precursor) molecules are not normally found as intracellular metabolites in the host organism or are present in low quantities. The present invention provides a method to produce or modify the composition or quantities of intracellular metabolites within a host organism where such metabolites are not naturally present or are present in non-optimal amounts.

A specific embodiment of the present invention concerns the introduction and modification of biochemical pathways for butyryl CoA biosynthesis. Butyryl CoA is a substrate utilized for the synthesis of 15-methyl-6-dEB by DEBS. The present invention provides methods to engineer a host organism so that it contains a new or modified ability to produce butyryl CoA and/or to increase or decrease the levels of butyryl CoA in the host, and the host cells thus modified.

A specific embodiment of the present invention concerns the additional introduction and modification of biochemical pathways for methylmalonyl CoA biosynthesis. Methylmalonyl CoA, as noted above, is a substrate (i.e., precursor) utilized for the synthesis of polyketides by many polyketide synthases. Some of the known biochemical pathways for the intracellular production of methylmalonyl CoA employ enzymes and their corresponding genes found in certain organisms. These enzymes and genes have not been found, or are otherwise non-optimal, in other organisms. These other organisms include those that could otherwise be very useful as heterologous hosts for the production of polyketides.

As noted above, two biochemical pathways involving methylmalonyl CoA are particularly relevant to this aspect of the present invention. These pathways are the methylmalonyl CoA mutase pathway, hereafter referred to as the MUT pathway, and the propionyl CoA carboxylase pathway, hereafter referred to as the PCC pathway.

The MUT pathway includes the enzymes methylmalonyl CoA mutase (5.4.99.2, using the numbering system devised by the Nomenclature Committee of the International Union of Biochemistry and Molecular Biology), methylmalonyl CoA epimerase (5.1.99.1), and malonyl CoA decarboxylase (4.1.1.9). The biochemical pathway includes the conversion of succinyl CoA to (R)-methylmalonyl CoA through the action of methylmalonyl CoA mutase (5.4.99.2) followed by the conversion of (R)-methylmalonyl CoA to (S)-methylmalonyl CoA through the action of methylmalonyl CoA epimerase (5.1.99.1). (S)-methylmalonyl CoA is a substrate (i.e., precursor) utilized by several polyketide synthases. The enzyme malonyl CoA decarboxylase (4.1.1.9) catalyzes the decarboxylation of malonyl CoA but is also reported to catalyze the decarboxylation of (R)-methylmalonyl CoA to form propionyl CoA. Propionyl CoA is a substrate (i.e., precursor) utilized by some polyketide synthases.

As an alternative to the mutase from, for example, *P. shermanii*, *S. coelicolor*, and *B. subtilis*, one can clone by PCR from *E. coli* genomic DNA the single gene for Sbm (sleeping beauty mutase), a methylmalonyl-CoA mutase that converts succinyl CoA to methylmalonyl CoA.

The PCC pathway includes the enzymes propionyl CoA carboxylase (6.4.1.3) and propionyl CoA synthetase (6.2.1.17). The biochemical pathway includes the conversion of propionate to propionyl CoA through the action of propionyl CoA synthetase (6.2.1.17) followed by the conversion of propionyl CoA to (S)-methylmalonyl CoA through the action of propionyl CoA carboxylase (6.4.1.3). (S)-methylmalonyl CoA is an extender unit utilized by many polyketide synthases. In one embodiment, the propionyl CoA carboxylase is a dimer encoded by the pccB and accA2 genes which have been characterized from *Streptomyces coelicolor* A3 by Rodriguez, E., et al., *Microbiology* (1999) 145:3109-3119. A biotin ligase activates these proteins, and aids biotin's attachment to the α (accA2) subunit of the propionyl-CoA carboxylase. *E. coli* birA (biotin ligase) gene under the ara promoter is described in Chapman-Smith, et al., *Biochem. J.* (1994) 302:881-887.

A suitable methylmalonyl CoA mutase (5.4.99.2) gene, a suitable methylmalonyl CoA epimerase (5.1.99.1) gene, a suitable malonyl CoA decarboxylase (4.1.1.9) gene, and a suitable propionyl CoA carboxylase (6.4.1.3) gene are found in U.S. patent application Ser. No. 09/699,136, which has been incorporated herein by reference.

An illustrative embodiment of the present invention employs specific enzymes from these pathways in addition to the enzymes in the ato pathway. As those skilled in the art will recognize upon contemplation of this description of the invention, the invention can also be practiced using additional and/or alternative enzymes involved in the MUT and PCC pathways. Moreover, the invention can be practiced using additional and alternative pathways for methylmalonyl CoA and other intracellular metabolites.

The methods of the invention involve the introduction of genetic material into a host strain of choice to modify or alter the cellular physiology and biochemistry of the host. Through the introduction of genetic material, the host strain acquires new properties, e.g. the ability to produce a new, or greater quantities of, an intracellular metabolite. In an illustrative embodiment of the invention, the introduction of genetic material into the host strain results in a new or modified ability to produce enzymes encoded by the ato pathway and the MUT pathway as shown in Example 1. The genetic material introduced into the host strain contains gene(s), or parts of genes, coding for one or more of the enzymes involved in the bio-synthesis of enzymes encoded by the ato operon and in the bio-synthesis of methylmalonyl CoA and may also include additional elements for the expression and/or regulation of expression of these genes, e.g., promoter sequences. Specific gene sequences coding for enzymes involved in the bio-synthesis of methylmalonyl CoA are in U.S. patent application Ser. No. 09/699,136, which has been incorporated herein by reference.

The invention also provides methods of producing polyketides using the host cells described above. The host cells of the invention may be cultured under conditions wherein a polyketide is produced. In some embodiments, the polyketide is an analog of 6-deoxyerythronolide B (6-dEB), modified by replacement of the propionate starter unit in the first step of polyketide synthesis in a host cell of the invention. Culture conditions for the production of a polyketide are known in the art. In some embodiments, the host cell is an *E. coli* cell modified to overexpress atoAD in order to increase production of non-propionyl CoA starter units, (e.g., butyryl CoA) and to express methylmalonyl CoA mutase and epimerase. In an illustrative embodiment, an *E. coli* cell is modified by the introduction of the genes for *Propionibacterium shermanii* methylmalonyl-CoA mutase (mutAB), the gene for *Streptomyces coelicolor* methylmalonyl-CoA epimerase and the gene for *E. coli* atoC by integrating these genes into the *E. coli* chromosome. Alternatively, the genes may be introduced by means of a non-integrating expression cassette. The host cell is co-transformed with genes encoding a PKS, e.g., the erythromycin PKS. The host cell is cultured under conditions such that the polyketide 15-methyl-6dEB is produced (e.g., by supplementing the medium with sodium butyrate, hydroxocobalamin (added in the dark), sodium glutamate, and sodium succinate). See Example 1, below. In another illustrative embodiment, the host cell is cultured under conditions such that the polyketide 14-Methylthio-6dEB is produced (e.g., by supplementing the medium with (methylthio) acetic acid, hydroxocobalamin (added in the dark), sodium glutamate, and sodium succinate). See Example 3, below.

A detailed description of the invention having been provided, the following examples are given for the purpose of illustrating the invention and shall not be construed as being a limitation on the scope of the invention or claims.

EXAMPLE 1

Production of 15-methyl-6-dEB in *E. coli* from an engineered mutase-epimerase-atoC pathway Integration of mutase-epimerase-atoC into the *E. coli* chromosome. To construct an *E. coli* strain able to produce (2S)-methylmalonyl-CoA from succinyl-CoA, and butyryl-CoA from butyrate, the genes for *Propionibacterium shermanii* methylmalonyl-CoA mutase (mutAB), the gene for *Streptomyces coelicolor* methylmalonyl-CoA epimerase (Dayem, et al., *Biochemistry*, 41:5193-201 (2002)) and the gene for *E. coli* atoC were integrated into the *E. coli* chromosome. The *E. coli* atoC gene is a transcriptional activator of the *E. coli* atoA and atoD genes, the products of which comprise an acyl-CoA transferase that, for example, transfers CoA from acetyl-CoA to butyrate. To construct the integration cassette, the genes were first cloned into intermediate vectors, placing each gene under control of a T7 promoter. The expression cassette containing mutase, epimerase and atoC was next inserted between ~2 kb of DNA homologous to the *E. coli* ygfG gene and sequences upstream and downstream of ygfG. The ygfG gene codes for a putative methylmalonyl-CoA decarboxylase; hence, integration into the ygfG locus will inactivate ygfG and abolish any ygfG-catalyzed methylmalonyl-CoA decarboxylase activity in *E. coli*. The DNA cassette containing the ygfG homology arms and metabolic pathway genes (see FIG. 1A) was introduced into the *E. coli* integration vector pKO3 (Link, et al., *J. Bacteriol*. 179:6228-37 (1997)), and the expression cassette was integrated into the ygfG locus in *E. coli* strain K173-145, as described by Link et al. (1997). The resulting strain, K214-37, contained the mutase-epimerase-atoC cassette shown in FIG. 1A integrated into the *E. coli* ygfG locus.

Production of 15-Me-6dEB. *E. coli* strain K214-37 was co-transformed with pKOS173-158, containing T7-eryA1 on a pET plasmid with kanamycin resistance, and with BP130 (Pfeifer, et al., *Science*), containing T7-eryA2, eryA3 on a pET plasmid with ampicillin resistance. Transformants were grown overnight at 37° C. in Luria-Bertani (LB) medium supplemented with 100 µg/ml carbenicillin (carb) and 50 µg/ml kanamycin (kan). Fresh LB medium (7 ml containing carb and kan in large culture tubes) was inoculated with 0.14 ml of overnight culture, and the culture was grown at 37° C. until it reached an OD of ~0.4, upon which the genes under control of the T7 promoter were induced with IPTG to 0.5 mM final concentration. The following components were added at the time of induction: sodium butyrate (5 mM final concentration), hydroxocobalamin (5 µM final concentration, added in the dark), sodium glutamate (50 mM final concentration), sodium succinate (50 mM final concentration). Following induction, the culture was grown at 22° C. in the dark. After 40 hours of growth, cells were collected by centrifugation, and 5 ml of supernatant was extracted with 5 ml of ethyl acetate. The ethylacetate containing the extracted polyketide was dried under vacuum, the residue was dissolved in methanol, and the extract was analyzed by LC/MS, and by LC with evaporative light scattering detection (ELSD). Polyketides in extracts were identified by LC/MS and quantified by ELSD (see Table 1).

TABLE 1

| 15-Me-6dEB via mutase | |
|---|---|
| Polyketide | mg/L culture |
| 15-Me-6dEB | 1 |
| 6dEB | <0.1 |

EXAMPLE 2

Production of 15-methyl-6-dEB in *E. coli* from an engineered PCC pathway

Integration of accA2 and pccB into the *E. coli* chromosome. To construct an *E. coli* strain able to produce (2S)-methylmalonyl-CoA from propionyl-COA, the genes for the two subunits of *S. coelicolor* propionyl-CoA carboxylase (PCC) were integrated into the *E. coli* chromosome. First, the genes were cloned into intermediate vectors, placing each gene under control of a T7 promoter. The expression cassette containing the PCC genes was next inserted between ~2 kb of DNA homologous to the *E. coli* ygfG gene, and sequences upstream and downstream of ygfG. The ygfG gene codes for a putative methylmalonyl-CoA decarboxylase; hence, integration into the ygfG locus will inactivate ygfG and abolish any ygfG-catalyzed methylmalonyl-CoA decarboxylase activity in *E. coli*. The DNA cassette containing the ygfG homology arms and PCC genes (see FIG. 1B) was introduced into the *E. coli* integration vector pKO3 [Link, et al. (1997)], and the expression cassette was integrated into the ygfG locus in *E. coli* strain K173-145, as described by Link, et al. (1997). The resulting strain, K207-3, contained the PCC cassette shown in FIG. 1B integrated into the *E. coli* ygfG locus. To produce butyryl-CoA from butyrate, the *E. coli* atoA and atoD genes were activated by expression of T7-atoC from the pACYC plasmid, pKOS214-004.

Production of 15-Me-6dEB. *E. coli* strain K207-3 was co-transformed with pKOS214-004 containing T7-atoC on a pACYC plasmid with tetracycline resistance, pKOS173-158, containing T7-eryA1 on a pET plasmid with kanamycin resistance, and with BP130 (Pfeifer, et al. *Science*), containing T7-eryA2, eryA3 on a pET plasmid with ampicillin resistance. Transformants were grown overnight at 37° C. in Luria-Bertani (LB) medium supplemented with 100 µg/ml carbenicillin (carb), 50 µg/ml kanamycin (kan), and 7.5 µg/ml tetracycline (tet). Fresh LB medium (25 ml containing carb, kan, tet in a 250 ml flask) was inoculated with 0.5 ml of overnight culture, and the culture was grown at 37° C. until it reached an OD of ~0.4, upon which the genes under control of the T7 promoter were induced with IPTG to 0.5 mM final concentration. The following components were added at the time of induction: sodium butyrate (10 mM final concentration), and sodium propionate (5 mM final concentration). Following induction, the culture was grown at 22° C. After 40 hours of growth, cells were collected by centrifugation, and 5 ml of supernatant was extracted with 5 ml of ethyl acetate. The ethylacetate fraction containing the extracted polyketide was dried under vacuum, the residue was dissolved in methanol, and the extract was analyzed by LC/MS, and by LC with evaporative light scattering detection (ELSD). Polyketides in extracts were identified by LC/MS and quantified by ELSD (see Table 2).

TABLE 2

15-Me-6dEB via PCC

| Polyketide | mg/L culture |
| --- | --- |
| 15-Me-6dEB | 0.25 |
| 6dEB | 3 |

EXAMPLE 3

Production of 14-desmethyl-14-(methylthio)-6-dEB in *E. coli* from an engineered mutase-epimerase-atoC pathway The mutase-epimerase-atoC cassette shown in FIG. 1C was introduced into a pACYC vector with tetracycline resistance to give pKOS207-15A.

*E. coli* strain K173-145 was co-transformed with pKOS207-15A (tet$^r$), pKOS173158, containing T7-eryA1 on a pET plasmid (kan$^r$), and with BP130 (Pfeifer, et al., *Science*), containing T7-eryA2, eryA3 on a pET plasmid (amp$^r$). Transformants were grown overnight at 37° C. in Luria-Bertani (LB) medium supplemented with 100 μg/ml carbenicillin (carb), 50 μg/ml kanamycin (kan), and 7.5 μg/ml tetracycline (tet). Fresh LB medium (25 ml containing carb, kan, tet in a 250 ml flask) was inoculated with 0.5 ml of overnight culture, and the culture was grown at 37° C. until it reached an OD of ~0.4, upon which the genes under control of the T7 promoter were induced with IPTG to 0.5 mM final concentration. The following components were added at the time of induction: (Methylthio)acetic acid (5 mM final concentration), hydroxocobalamin (5 μM final concentration, added in the dark), sodium glutamate (50 mM final concentration), sodium succinate (50 mM final concentration). Following induction, the culture was grown at 22° C. in the dark. After 40 hours of growth, cells were collected by centrifugation and 5 ml of supernatant was extracted with 5 ml of ethyl acetate. The ethylacetate containing the extracted polyketide was dried under vacuum, the residue was dissolve in methanol, and the extract was analyzed by LC/MS. The LC/MS analysis demonstrated that 14-desmethyl-14-(methylthio)-6-dEB was produced (<0.5 mg polyketide/L culture).

Although the present invention has been described in detail with reference to specific embodiments, those of skill in the art will recognize that modifications and improvements are within the scope and spirit of the invention, as set forth in the claims which follow. All publications and patent documents cited herein are incorporated herein by reference as if each such publication or document was specifically and individually indicated to be incorporated herein by reference. Citation of publications and patent documents is not intended as an admission that any such document is pertinent prior art, nor does it constitute any admission as to the contents or date of the same. The invention having now been described by way of written description and example, those of skill in the art will recognize that the invention can be practiced in a variety of embodiments and that the foregoing description and examples are for purposes of illustration and not limitation of the following claims.

The invention claimed is:

1. A recombinant host cell that produces a polyketide using a starter unit, wherein the recombinant host cell is derived from a native host cell by modification with an expression vector, wherein said expression vector expresses or overexpresses an atoAD enzyme and wherein increased expression of the atoAD enzyme results in increased production of the starter unit, wherein the atoAD enzyme is an acetyl-CoA acetoacetate: CoA transferase enzyme designated EC 2.8.3.8.

2. The host cell of claim 1, further modified to express methylmalonyl-CoA mutase and methylmalonyl-CoA epimerase.

3. The host cell of claim 1 wherein the starter unit is selected from the group consisting of acetyl CoA, butyryl CoA, 3-fluoropropionyl CoA, 3-chloropropionyl CoA, 3,3,3-trifluoropropionyl CoA, 3-hydroxypropionyl CoA, fluoroacetyl CoA, lactyl CoA, (methylthio)acetyl CoA, chloroacetyl CoA, glycolyl CoA, 4-chlorobutyryl CoA, 2-methylbutyryl CoA, and valeryl CoA.

4. The host cell of claim 3 wherein the starter unit is selected from the group consisting of acetyl CoA, butyryl CoA, (methylthio)acetyl CoA, 4-chlorobutyryl CoA, 2-methylbutyryl CoA, and valeryl CoA.

5. The host cell of claim 3 wherein the starter unit is butyryl CoA or (methylthio)acetyl CoA.

6. The host cell of claim 1 that is an *Escherichia coli* host cell.

7. The host cell of claim 3 that is an *Escherichia coli* host cell.

8. The host cell of claim 1 that is a yeast host cell.

9. The host cell of claim 1, wherein the polyketide is synthesized by a modular polyketide synthase (PKS).

10. The host cell of claim 1, wherein the polyketide is an analog of 6-deoxyerythronolide B (6-dEB) modified by replacement of the propionate starter unit.

11. The host cell of claim 10, wherein the polyketide is selected from the group consisting of 14-desmethyl-6-dEB, 15-methyl-6-dEB, 15-fluoro-6-dEB, 15-chloro-6-dEB, 15-trifluoro-6-dEB, 15-hydroxy-6-dEB, 14-desmethyl-14-fluoro-6-dEB, 14-hydroxy-6-dEB, 14-desmethyl-14-(methylthio)-6-dEB, 14-desmethyl-14-chloro-6-dEB, 14-desmethyl-14-hydroxy-6-dEB, 15-(chloromethyl)-6-dEB, 14-ethyl-6-dEB, and 15-ethyl-6-dEB.

12. The host cell of claim 10 wherein the polyketide is 15-methyl-6-dEB or 14-desmethyl-14-(methylthio)-6-dEB.

13. The host cell of claim 2 which has been further modified to overexpress a B12 transporter gene.

14. The host cell of claim 1, further modified to express propionyl-CoA carboxylase.

15. A method for producing an analog of 6-deoxyerythronolide B (6-dEB) modified by replacement of the propionate starter unit in a host cell of claim 1, comprising culturing the host cell under conditions wherein the analog of 6-dEB is produced, and wherein said analog is 14-desmethyl-6dEB, 15-methyl-6-dEB, 15-fluoro-6-dEB, 15-chloro-6-dEB, 15-trifluoro-6-dEB, 15-hydroxy-6-dEB, 14-desmethyl-14- fluoro-6-dEB, 14-hydroxy-6-dEB, 14-desmethyl-14-(methylthio)-6-dEB, 14-desmethyl-14-chloro-6-dEB, 14-desmethyl-14-hydroxy-6-dEB, 15-(chloromethyl)-6-dEB, 14-ethyl-6-dEB, or 15-ethyl-6-dEB.

16. The host cell of claim 14, further modified to overexpress a biotin ligase enzyme.

17. The host cell of claim 16 wherein the biotin ligase enzyme is encoded by the birA gene.

* * * * *